(12) United States Patent
Pike et al.

(10) Patent No.: US 6,207,637 B1
(45) Date of Patent: Mar. 27, 2001

(54) DISULFONATED ALKYLAMINES AS DEGREASERS AND HYDROTROPES

(75) Inventors: Philip W. Pike, Concord; Bryan A. Grisso, Wickliffe; Richard W. Jahnke, Mentor, all of OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 09/177,995

(22) Filed: Oct. 23, 1998

(51) Int. Cl.$^7$ .................................................. C11D 1/28
(52) U.S. Cl. ........................ 510/494; 510/495; 554/48; 562/102
(58) Field of Search .................................. 510/494, 495; 554/48; 562/102

(56) References Cited

U.S. PATENT DOCUMENTS

| | | | |
|---|---|---|---|
| 5,079,081 | 1/1992 | Lal | 428/290 |
| 5,101,012 | 3/1992 | Lal | 528/337 |
| 5,115,083 | 5/1992 | Piedrahita et al. | 528/230 |
| 5,266,237 | 11/1993 | Freeman et al. | 252/524 |
| 5,607,618 | 3/1997 | Antwerpen et al. | 510/302 |

FOREIGN PATENT DOCUMENTS

| | | | |
|---|---|---|---|
| 1329565 | 9/1973 | (GB) | 143/14 |
| 1550420 | 8/1979 | (GB) | 143/675 |

*Primary Examiner*—John Hardee
(74) *Attorney, Agent, or Firm*—David M. Shold; Michael F. Esposito

(57) ABSTRACT

The reaction product of an alkylenediamine, each amino group thereof being a primary or secondary amino group; with at least two equivalents of an acrylamidoalkanesulfonic acid or a salt thereof, wherein each amine nitrogen atom of said alkylenediamine is reacted with a single molecule of the acrylamidoalkane sulfonic acid or salt thereof provides a useful surfactant or hydrotrope.

27 Claims, No Drawings

DISULFONATED ALKYLAMINES AS DEGREASERS AND HYDROTROPES

BACKGROUND OF THE INVENTION

The present invention relates to compositions based on the reaction product of an alkylenediamine with at least two equivalents of an acrylamidoalkanesulfonic acid or a salt thereof, and formulations containing such material. Such aqueous solutions or dispersions are useful for cleaning soiled articles or surfaces, e.g., for degreasing.

A variety of reaction products of acrylamidoalkanesulfonic acids are known for various uses. British Patent 1,550,420, Aug. 15, 1979, discloses aminodi- and aminopolyalkylamidoalkane sulfonic acids and salts of the formula

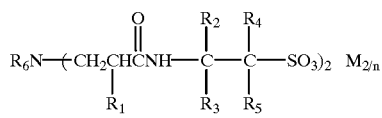

$R_6$ can be a group derived from a polyvalent amine, such as

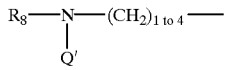

where Q' is $-[-CH_2CHR_1-C(=O)-NH-CR_2R_3CR_4R_5-SO_3]_nM$

U.S. Pat. No. 5,115,083, Piedrahita et al., May 19, 1992, discloses catalysts for curing aminoplast compositions. One such catalyst is an acid, or an ammonium or metal salt of a reaction product of at least one amine and a sulfo compound. Sulfo compounds include 2-acrylamido-2-methylpropane sulfonic acid. The amines can be primary or secondary amines, and react by the Michael addition. Exemplified amines are 2-amino-2-methylpropanol and triethyl amine. Other amines include alkylene polyamine represented by the formula

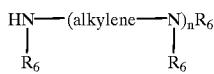

$R_6$ is independently preferably hydrogen; or an aliphatic or hydroxy-substituted aliphatic group of up to about 30 carbon atoms.

U.S. Pat. No. 5,079,081, Lal, Jan. 7, 1992, and related U.S. Pat. No. 5,101,012, Mar. 31, 1992, disclose compositions and polymer fabrics treated therewith. The composition is prepared by reacting (a) the reaction product of a hydrocarbyl substituted carboxylic acid or anhydride and a polyamine, wherein the reaction product has at least one NH group capable of addition to a double bond, with (b) a sulfo compound such as 2-acrylamido-2-methylpropane sulfonic acid. The sulfo compound is reacted with the amine-containing compound at an equivalent ratio of about (1:1–10), preferably about (1:1–1.1).

SUMMARY OF THE INVENTION

In one embodiment, the present invention provides a composition of matter which is the reaction product of an alkylenediamine, each amino group thereof being a primary or secondary amino group; with at least two equivalents of an acrylamidoalkanesulfonic acid or a salt thereof, wherein each amine nitrogen atom of said alkylenediamine is reacted with a single molecule of the acrylamidoalkane sulfonic acid or salt thereof. In one embodiment, the subject composition can be represented by the structure

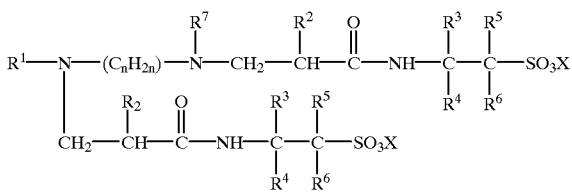

wherein n is 2 to 6; $R^1$ and $R^7$ are each independently hydrogen, hydrocarbyl groups, hydroxyhydrocarbyl groups, alkoxyhydrocarbyl groups, aminohydrocarbyl groups, aminohydrocarbyl groups wherein the amine nitrogen is substituted by

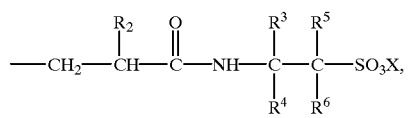

alkoxy-terminated or amine-terminated polyether groups, or a mixture thereof; $R^2$ through $R^6$ are each independently hydrogen or hydrocarbyl groups, and each X is independently hydrogen, metal, or ammonium or substituted ammonium.

The present invention further provides a method of cleaning a soiled article or surface, comprising contacting with said article or surface an aqueous solution or dispersion of a composition of matter represented by the structure

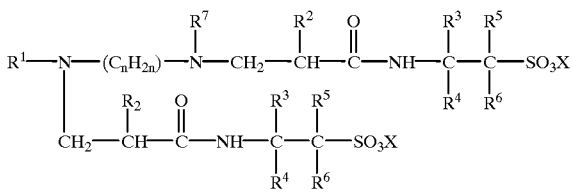

wherein n is 2 to 6; $R^1$ and $R^7$ are each independently hydrogen, hydrocarbyl groups, hydroxyhydrocarbyl groups, alkoxyhydrocarbyl groups, aminohydrocarbyl groups, aminohydrocarbyl groups wherein the amine nitrogen is substituted by

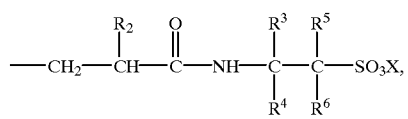

alkoxy-terminated or amine-terminated polyether groups, additional groups of the structure

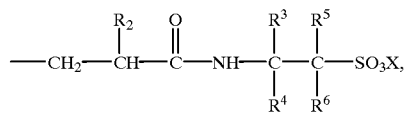

or mixtures thereof; $R^2$ through $R^6$ are each independently hydrogen or hydrocarbyl groups; and each X is independently hydrogen, metal, or ammonium or substituted ammonium.

DETAILED DESCRIPTION OF THE INVENTION

Various preferred features and embodiments will be described below by way of non-limiting illustration.

In one embodiment, the composition which is a subject of the present invention is the reaction product of an alkylenediamine, each amino group thereof being a primary or secondary amino group; with at least two equivalents of an acrylamidoalkanesulfonic acid or a salt thereof, wherein each amine nitrogen atom of said alkylenediamine is reacted with a single (that is, one) molecule of the acrylamidoalkane sulfonic acid or salt thereof.

Alkylene diamines are well known materials having a general structure $H_2N\text{-}(C_nH_{2n})\text{-}NH_2$ in their unsubstituted form. In this formula, n is a number of at least 2, generally 2 through 6, preferably 2 through 4, and in one preferred embodiment, 3. Such materials correspond to ethylene diamine, propylene diamines, butylene diamines, pentylene diamines, and hexylene diamines (such as hexamethylene diamine), and include both the normal or linear materials as well as the branched materials. The nitrogen atoms can be located in the $\alpha,\beta$ positions or in other positions such as the $\alpha,\omega$ positions, as in the case of 1,3-propylene diamine, which is a preferred material.

The diamine in the present invention is preferably an N-substituted alkylenediamine, that is, one in which one hydrogen atom of one or of both of the nitrogen atoms is replaced by an atom other than hydrogen. The substituted alkylenediamine can then be represented by the structure $R^1NH\text{-}(C_nH_{2n})\text{-}NHR^7$, where $R^1$ and $R^7$ are each independently hydrogen, hydrocarbyl groups, hydroxyhydrocarbyl groups, alkoxyhydrocarbyl groups, aminohydrocarbyl groups, aminohydrocarbyl groups wherein the amine nitrogen is substituted by

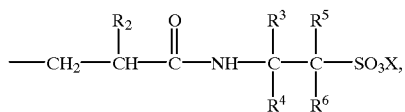

alkoxy-terminated or amine-terminated polyether groups, or a mixture thereof. For the substituted material, at least one of $R^1$ and $R^7$ is other than hydrogen. If $R^1$ or $R^7$ contain an amino group, then by a strict definition the overall molecule might not be called a "diamine," yet for the purposes of the present invention, such materials will be considered to be diamines.

In the preferred material, the diamine is monosubstituted by a hydrocarbon group or an alkoxyalkyl group such as an alkoxypropyl group. The preferred hydrocarbon substituent is an aliphatic hydrocarbon group containing 1 to 30 carbon atoms, preferably 4 to 24 carbon atoms, more preferably 8 to 18 carbon atoms. In one embodiment, $R^1$ can be the hydrocarbon group or mixture of hydrocarbon groups corresponding to the hydrocarbon portion of cocoamine, tallowamine, or oleylamine. The length of the hydrocarbon substituent will affect to some extent the properties of the resulting compound. When a relatively long hydrocarbon substituent is used, e.g., having 10 or 12 to 18 or more carbon atoms, the hydrocarbon portion will impart a measure of hydrophobic character to the composition and the composition will tend to have the properties of a surfactant. When a relatively short hydrocarbon substituent is used, e.g., having 4 to 10 or 12 carbon atoms, the composition will have the properties of a hydrotrope, that is, a material which can serve to increase the solubility of a nonionic surfactant in a formulation.

In a preferred embodiment, the N-substituted alkylenediamine is a mono-N—$C_{10\text{-}18}$ hydrocarbon-substituted propylene diamine. In another preferred embodiment, the N-substituted alkylenediamine is a mono-N—$C_{4\text{-}10}$ hydrocarbon-substituted propylene diamine.

The diamine is reacted with at least two equivalents of an acrylamidoalkanesulfonic acid or a salt thereof. Acrylamidoalkanesulfonic acids and salts are materials represented by the formula

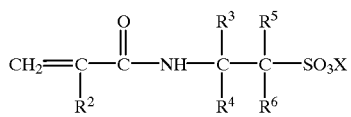

in which $R^2$ through $R^6$ are each independently hydrogen or hydrocarbyl groups, and X is hydrogen, metal, or ammonium or substituted ammonium. In the preferred embodiments, $R^2$ is hydrogen or a lower hydrocarbyl or alkyl radical and each of $R^4$, $R^5$, and $R^6$ is independently hydrogen or an alkyl or hydrocarbyl radical, and $R^3$ is hydrogen, an alkyl or hydrocarbyl radical, or an $SO_3H$-substituted alkyl group. The term "lower" as used in this context designates radicals containing up to 7 carbon atoms. The term "acrylamidoalkanesulfonic acid" thus includes derivatives of methacrylic acid (where $R^2$ is methyl), ethacrylic acid, and the like, and not just acrylic acid. Preferably the alkyl group $R^2$ has 6 or fewer carbon atoms, more preferably 3 or fewer carbon atoms. More preferably yet $R^2$ is methyl, and most preferably it is hydrogen.

In the above formulas, X is preferably ammonium or an alkali or alkaline earth metal ion. More preferably X is ammonium, sodium, magnesium, or calcium.

Preferably each of $R^2$, $R^3$, $R^4$, $R^5$, and $R^6$ is hydrogen or a lower alkyl radical. In a preferred embodiment, $R^3$ and $R^4$ are methyl, while $R^2$, $R^5$, and $R^6$ are hydrogen. Such a material is 2-acrylamido-2-methylpropane sulfonic acid, represented by the formula

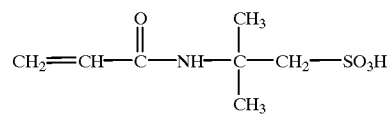

(The commercial grade material is believed to include a fraction containing two sulfonic acid groups, that is, where $R^3$ is a —$CH_2SO_3H$ group.) This material is commercially available from The Lubrizol Corporation as AMPS® monomer, and from Toa Gosei under the trade name "ATBS." Other useful materials of this class include 2-acrylamidoethanesulfonic acid, 2-acrylamidopropanesulfonic acid, 2-methacrylamidopropanesulfonic acid, and 2-methacrylamido-2-methylpropanesulfonic acid. Such materials and their methods of preparation are disclosed, for instance, in U.S. Pat. No. 3,544,597.

The diamine and the acrylamidoalkanesulfonic acid are preferably reacted in amounts and under conditions such that each of the two amine nitrogen atoms of the diamine is predominantly reacted with exactly one molecule of the sulfonic acid. The reaction is sometimes referred to as a Michael addition. Suitable conditions leading to the controlled degree of reaction characteristic of the present invention include combining the diamine and at least 2 moles of acrylamidoalkanesulfonic acid in a suitable solvent (such as water and/or alcohols) at a temperature of 40 to 130° C., preferably 70 to 100° C. for 4 to 30 hours. The total concentration of the reactants can be 1 to 50% by weight, preferably 5 to 30% by weight. Optionally, a free radical inhibitor such as monomethoxyhydroquinone can be used at a suitable concentration such as about 1000 parts per million. However, in some cases a product will be prepared which is a mixture of material containing some of the adduct in which two acrylamidoalkanesulfonic acid groups have added to one of the nitrogen atoms. Thus, the preferred adduct will be represented by the structure

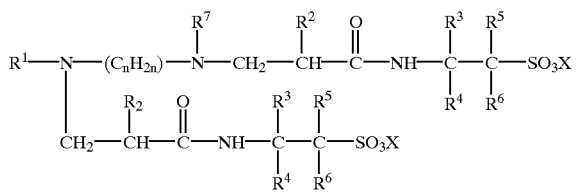

and the alternative structure which may also be present, preferably in minor amounts, can be represented by

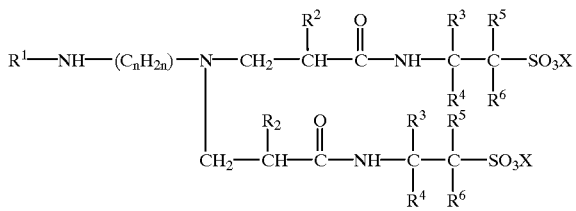

A similar structure in which three acrylamidoalkanesulfonic acid groups have added to the structure (i.e., the third such group replacing the hydrogen atom on the leftmost nitrogen group in the immediately preceding structure) can also be present in minor amounts.

In the above structures, $R^1$, $R^7$, and n are as earlier defined. $R^2$ through $R^6$ and X are each likewise as earlier defined.

Another embodiment of the present invention provides a solution or dispersion of (a) one or more of the above-described compositions in (b) water. The amount of the component (a) is an amount sufficient to provide reduced surface tension, hydrotropic performance, or cleaning performance to the solution or dispersion, and is generally 0.01 to 50 percent by weight, preferably 0.1 to 25 percent by weight of the solution or dispersion. If the composition is used as a concentrate, higher concentrations of component (a) will be present; if it is used as a final cleaning product, relatively lower concentrations will be used. The component (a) can be used as the principal surfactant in the mixture, in which case it will typically be present in an amount of 0.1 to 25 percent by weight, preferably 0.5 to 10 percent, and more preferably 1 or 3 to 6 percent. The composition can contain an additional, non-ionic, surfactant, if desired. In that case, the component (a) can be employed as a hydrotrope, in which case its concentration will typically be 0.1 to 3 percent by weight, preferably 0.5 to 2 percent. Alternatively expressed, component (a) will be present in an amount suitable to increase the solubility of the non-ionic surfactant in the solution or dispersion. The amount of the additional surfactant, if present, will typically be 0.01 to 25 percent by weight, preferably 0.1 to 10 percent, more preferably 1 to 5 percent.

The compositions of this invention have shown improved hydrotropic efficiency compared to several commercial surfactants (hydrotropes). Lower concentrations can be used to raise the cloud point of a cleaner composition containing a non-ionic surfactant. Cleaner formulations containing these compositions perform favorably compared to commercially available anionic surfactants.

The compositions of the present invention also find use in a number of areas including as foam control agents, emulsifiers, dispersion aids, anticaking aids, and cleaners. The proper amounts and concentrations for each application will be apparent to those skilled in the art.

The materials of the present invention can also be used to modify the viscosity characteristics of either nonionic or anionic surfactants, especially when such surfactants are present in relatively high concentrations (e.g., up to 50% by weight).

The present invention also contemplates a method of cleaning a soiled article or surface, comprising contacting with said article or surface an aqueous solution or dispersion of a composition of matter represented by the structure

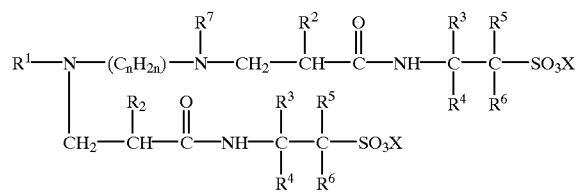

wherein n is 2 to 6; $R^1$ and $R^7$ are each independently hydrogen, hydrocarbyl groups, hydroxyhydrocarbyl groups, alkoxyhydrocarbyl groups, aminohydrocarbyl groups, aminohydrocarbyl groups wherein the amine nitrogen is substituted by

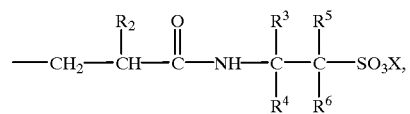

alkoxy-terminated or amine-terminated polyether groups, additional groups of the structure

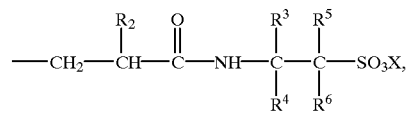

or mixtures thereof; $R^2$ through $R^6$ are each independently hydrogen or hydrocarbyl groups; and each X is independently hydrogen, metal, or ammonium or substituted ammonium.

When the compositions, and in particular the aqueous solutions or dispersions of the present invention are used as cleaners, they are typically employed in a customary manner, including customary temperatures (e.g., room temperature or elevated temperatures). That is, the composition is contacted with a soiled article or surface, optionally with agitation or rubbing, and then the composition is removed, along with a suitable portion of the soiling material. When the article is a woven or fibrous material, article, washing can be accomplished as in a customary home or industrial washing machine. When the material to be washed is comprises a solid surface (glass, metal, wood, or the like), the cleaning composition can be applied to the surface and rubbed, sprayed, or rinsed off, either manually or automatically (as in a dishwasher). In a preferred embodiment, for which the compositions of the present invention are particularly suited, the soiled article or surface is a steel surface which is soiled with a soilant which comprises an oil such as mineral oil or vegetable oil.

Cleaners which employ the materials of the present invention can also include other conventional additives such as alcohols, glycerin, water-insoluble solvents, polymers, antioxidants, bactericides, corrosion inhibitors, fragrances, fabric softening agents, anti-foam agents, nonionic, anionic, cationic, or zwitter-ionic surfactants, soaps, acids or other pH adjusting agents, siloxanes, dyes or pigments, sequestering agents, optical brighteners, enzymes, bleaching agents, and anti-redeposition agents.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a pre-dominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

It is known that some of the materials described above may interact in the final formulation, so that the components of the final formulation may be different from those that are initially added. For instance, metal ions (of, e.g., a detergent) can migrate to other acidic sites of other molecules. The products formed thereby, including the products formed upon employing the composition of the present invention in its intended use, may not be susceptible of easy description. Nevertheless, all such modifications and reaction products are included within the scope of the present invention; the present invention encompasses the composition prepared by admixing the components described above.

EXAMPLES

Example 1

Preparation Of 1:1 Adduct.

To a 2 L flask equipped with condenser, stirrer, and thermowell is charged 500 g methanol, 568.4 g (1.44 equivalents) of an aqueous solution of the sodium salt of 2-acrylamido-2-methylpropanesulfonic acid, and 200 g (1.55 equivalents) of N—$C_{12}$ alkyl (coco)-1,3-propylenediamine (Duomeen C™). The mixture is stirred and heated to reflux at about 75° C., without the use of nitrogen blanket. Reflux conditions are maintained for 30 hours. At the conclusion of the heating time, methanol and water are removed from the reaction mixture using a vacuum oven while maintaining the temperature below 100° C. The product is 445 g of a hygroscopic yellowish solid.

Example 2

To a 500 mL flask are charged 39.5 g of the aqueous solution of the sodium salt of 2-acrylamido-2-methylpropanesulfonic acid (58% solids in solution), 16.1 g Duomeen T™ (a diamine similar to that of example 1, in which the alkyl group is a predominantly $C_{16}$–$C_{18}$ alkyl group based on tallowamine) 350 g water, and 0.1 g hydroquinone monomethoxy ether (inhibitor). The mixture is stirred at 95° C. for 16 hours. At the end of this time a homogeneous solutions results. The water is removed from the mixture as in Example 1, leaving a dull orange solid product, which is very water soluble.

Example 3

To a flask is charged 39.5 g (0.1 equivalents) of an aqueous solution of the sodium salt of 2-acrylamido-2-methylpropanesulfonic acid, 300 g water, and 0.1 g hydroquinone monomethoxy ether (inhibitor), and 13.9 g (0.1 equivalent) Duomeen C™. The mixture is warmed to 95° C. with stirring and maintained at temperature for 16 hours. Water is removed from the resulting solution as in Example 1, providing a dull yellow powder which is very water soluble.

Example 4

To a flask is charged 39.5 g (0.1 equivalents) of an aqueous solution of the sodium salt of 2-acrylamido-2-methylpropanesulfonic acid, 69.3 g water, and 0.1 g hydroquinone monomethoxy ether (inhibitor), followed by 13.9 g (0.1 equivalent) Duomeen C™. The mixture is warmed to 95° C. with stirring and maintained at temperature for 30 hours. The resulting solution is a clear yellow liquid, containing 70% water, which does not require filtration. Evaluation by $^1$H—NMR indicates only 1% unreacted olefin.

Example 5

To a 500 mL flask are added 39.5 g of an aqueous solution of the sodium salt of 2-acrylamido-2-methylpropanesulfonic acid, 16.3 g (0.1 equivalents) of Duomeen OL™, a diamine in which the alkyl group is a predominantly $C_{18}$ unsaturated group based on oleylamine, 350 mL water, and 0.01 g hydroquinone monomethoxy ether (inhibitor). The mixture is stirred at 95° C. for 16 hours, whereupon the mixture is a homogeneous solution. Water is removed from the resulting solution as in Example 1, providing a powder which is very water soluble.

Example 6

Example 1 is substantially repeated except that the Duomeen C™ is replaced with an equivalent amount of Tomah DA-16™, a diamine represented by the formula R—O—$CH_2CH_2CH_2NH$—$CH_2CH_2CH_2NH_2$, where R is an isododecyl group.

Example 7

Into a flask is placed 22.9 g (0.1 moles) of the sodium salt of 2-acrylamido-2-methylpropanesulfonic acid, dissolved, if desired, in an appropriate solvent, along with sufficient water to bring the final product mixture to 70% water and 30% total solids. Ethylene diamine (6.0 g; 0.1 moles) is added to the reaction mixture. The mixture is warmed to 95° C. and maintained at that temperature for 30 hours to provide a solution which is used without filtration. The progress of the reaction is followed by infrared spectroscopy.

Examples 8–14: Hydrotropic Activity

The effect of the materials of the present invention as hydrotropes is determined by measuring their effect on the cloud point of a surfactant composition. Cloud point is determined by the procedure of ASTM-D-2024-65; higher cloud points (which are generally desirable) indicate that a composition may be used at a relatively higher temperature without the development of cloudiness. Two surfactant concentrates are prepared, "Mild" Alkaline Cleaner, and "Strong" Alkaline Cleaner, as follows:

| "MILD" | "STRONG" |
| --- | --- |
| 5% Alcohol ethoxylate (Berol ™ 535) | 5% Alcohol ethoxylate (Berol ™ 535) |
| 10% Tetrapotassium pyrophosphate | 6% Tetrapotassium pyrophosphate |
| — | 3% Sodium metasilicate |
| 2.5% (or as indicated) Test Material | 3% (or as indicated) Test Material |
| balance: Water | balance: Water |

In the absence of added "Test Material" in the formulations, the cloud point of each concentrate is 20° C.

Ex. 8

When the material of Example 1 (i.e., the product of 2-5 acrylamido-2-methylpropanesulfonic acid and Duomeen C™ in a 1:1 equivalent ratio) is added as the "Test Material," the cloud point is increased to greater than 90° C.

Ex. 9, 10, 11

When very low concentrations (0.1%) of the materials of Examples 1, 2 and 4 (each prepared at a 1:1 equivalent ratio), are added as the "Test Material" to the "Strong" Alkaline Cleaner, the cloud point is measured at 58° C.,>100° C., and >100° C., respectively.

Ex. 12, 13, 14

When the materials of Examples 1, 2, and 5 (1:1 equivalent ratio in each case) are added to the "Mild" Alkaline Cleaner, the cloud points below are measured at the concentrations indicated:

| Test Material | % Added | Cloud point, ° C. |
| --- | --- | --- |
| Ex. 1 | 2.1 | 52 |
| Ex. 2 | 0.6 | 68 |
| Ex. 4 | 0.5 | 68 |

These results are considered to represent very good hydrotropic activity.

Example 15—Cleaning Performance.

Unglazed ceramic tiles are broken up into small pieces approximately cubic, measuring 10–15 mm on a side. The pieces are coated with a soilant of saturated and unsaturated fats containing a water-soluble dye. Deionized water containing 5 weight percent of a surfactant concentrate is added and the mixture shaken at room temperature for 10 minutes. The cleaning solution is poured off and the ceramic is rinsed with deionized water. After weighing the percentage soil removed is determined.

The concentrate comprises 7.5 weight percent of the 1:1 adduct of the sodium salt of 2-acrylamido-2-methylpropanesulfonic acid and either Duomeen C™ (concentrate (a)) or Duomeen T™ (concentrate (b)); in each case with 3 weight percent sodium metasilicate, 3 weight percent sodium pyrophosphate, and 86.5 weight percent deionized water. The cleaning results are shown in the following table:

| Concentrate | % Soil Removal |
| --- | --- |
| a | 61 |
| b | 64 |

Examples 16–24

"Strong" Alkaline Cleaner formulations reported above, containing 3% of the materials of Examples 1, 2, and 5 (1:1 equivalent ratio compositions). The formulations are diluted 20:1 with water and used in cleaning and degreasing experiments. Steel plates are contaminated with "Lorry Dirt" (a combination believed to comprise engine oil, mineral oil, bitumen, and other contaminants, obtained from the exterior of a truck/lorry) or lard. The contaminated steel plates are immersed in the cleaning solution for 10 minutes at 25° C., followed by rinsing with distilled water. The degreasing ability is measured by total carbon analysis, as indicated.

(The total carbon analysis is performed by the Institute for Metal Research Combustion [MRC] method, which is based on the oxidation of compounds by a flowing stream of oxygen in a furnace. The temperature of the furnace is increased at a defined rate from room temperature to a pre-set value, and the carbon compounds or the oxidized compounds on the surface evaporate in an order depending on the stability and volatility of the compound. Upon exiting the furnace, the gases are completely oxidized to carbon dioxide and water and these gases analyzed in an IR detector.)

| Test Material | Lorry Dirt MRC (mg/m$^2$) | Lard MRC (mg/m$^2$) |
| --- | --- | --- |
| none (reference) | ca. 380 | ca. 800 |
| Ex. 1 | 22, 12 | 100, 50 |
| Ex. 2 | 15, 12 | 250, 50 |
| Ex. 5 | 19, 18 | 500, 60 |

Each of the values in the above table is estimated as accurate within +/−10% (Analysis of the degreasing ability on the samples contaminated with Lard, expressed as percent contamination remaining by gravimetric analysis, gives the following results: reference, 22%, 16%; material of Ex. 1: 64%, 46%; material of Ex. 2: 68%, 58%; material of Ex. 5: 70%, 65%. The anomalous performance by gravimetric analysis not understood.)

Examples 25 and 26.

Both "Mild" and "Strong" Alkaline Cleaner formulations as reported above, containing 2.5% and 3%, respectively of the material of Example 1 (1:1 equivalent ratio composition) are prepared. The formulations are diluted 20:1 with water and used in degreasing experiments. Steel plates are contaminated with gear oil (from Valvoline) and heated to 50° C. for 3 hours. The contaminated steel plates are immersed in the cleaning solution and agitated for 10 minutes at 25° C. in a shaking bath, followed by rinsing with distilled water for 10 minutes in a shaking bath. The degreasing ability as measured by total carbon analysis is reported below:

| Composition | Residual C (mg/m²) |
|---|---|
| "Mild" | 31, 22 |
| "Strong" | 19, 14 |

Each of the values in the above table is estimated as accurate within +/−10%.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A composition of matter represented by the structure

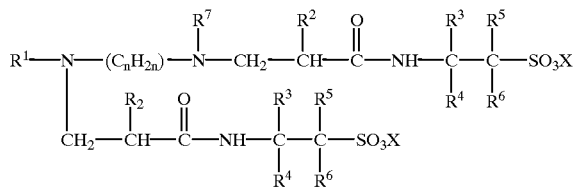

wherein n is 2 to 6; $R^1$ and $R^7$ are each independently hydrogen, hydrocarbyl groups, hydroxyhydrocarbyl groups, alkoxyhydrocarbyl groups, (aminohydrocarbyl groups, aminohydrocarbyl groups wherein the amine nitrogen is substituted by

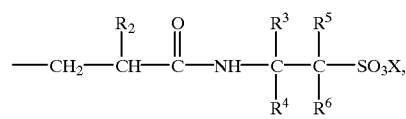

alkoxy-terminated or amine-terminated polyether groups, or a mixture thereof; $R^2$ through $R^6$ are each independently hydrogen or hydrocarbyl groups, and each X is independently hydrogen, metal, or ammonium or substituted ammonium.

2. The composition of claim 1 wherein n is 2 to 4.
3. The composition of claim 1 wherein n is 3.
4. The composition of claim 1 wherein $R^1$ is a hydrocarbon group or an alkoxypropyl group and $R^7$ is hydrogen.
5. The composition of claim 1 wherein $R^1$ is an aliphatic hydrocarbon group containing 1 to about 30 carbon atoms.
6. The composition of claim 5 wherein $R^1$ contains about 4 to about 10 carbon atoms.
7. The composition of claim 5 wherein $R^1$ contains about 10 to about 18 carbon atoms.
8. The composition of claim 1 wherein $R^2$ is hydrogen.
9. The composition of claim 1 wherein $R^3$ and $R^4$ are methyl and $R^5$ and $R^6$ are hydrogen.
10. The composition of claim 1 wherein X is an alkali metal or an alkaline earth metal.
11. The composition of claim 1 wherein X is sodium, calcium, or magnesium.
12. The composition of claim 1 wherein X is ammonium or substituted ammonium.
13. The composition of claim 1 wherein the composition is represented by the structure

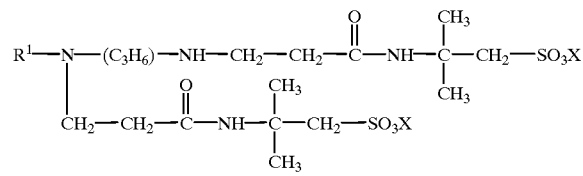

14. The compostion of claim 13 wherein $R^1$ is the hydrocarbon group or mixture of hydrocarbon groups corresponding to the hydrocarbon portion of cocoamine, tallowamine, or oleylamine.
15. The composition of claim 13 wherein $R^1$ is an alkyl group containing 4 to 12 carbon atoms.
16. The composition of claim 1 admixed with a composition represented by the structure

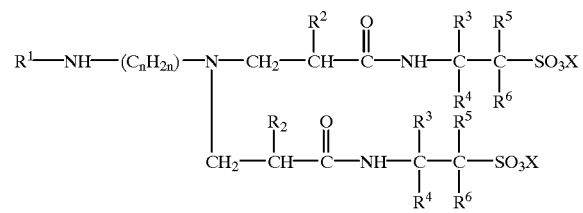

where n, $R^1$ through $R^6$ and X are as defined in claim 1.

17. The reaction product of an alkylenediamine, each amino group thereof being a primary or secondary amino group; with at least two equivalents of an acrylamidoalkanesulfonic acid or a salt thereof, wherein each amine nitrogen atom of said alkylenediamine is reacted with a single molecule of the acrylamidoalkane sulfonic acid or salt thereof.
18. The reaction product of claim 17 wherein the alkylenediamine is a mono-N-$C_{10-18}$ hydrocarbon-substituted propylenediamine.
19. The reaction product of claim 17 wherein the alkylenediamine is a mono-N-$C_{4-10}$ hydrocarbon substituted propylenediamine.
20. The reaction product of claim 17 wherein the acrylamidoalkanesulfonic acid or salt thereof is 2-acrylamido-2-methylpropanesulfonic acid or a salt thereof.
21. The reaction product of claim 20 wherein the salt is a sodium, calcium, magnesium, or ammonium salt.

22. A solution or dispersion of (a) the composition of claim 1 in (b) water.

23. The aqueous solution or dispersion of claim 22 wherein the amount of component (a) is about 0.01 to about 50 percent by weight of the solution or dispersion.

24. The aqueous solution or dispersion of claim 22 further comprising (c) a non-ionic surfactant, wherein the amount of component (a) is an effective amount to increase the solubility of the non-ionic surfactant in said solution or dispersion.

25. The aqueous solution or dispersion of claim 24 wherein the amount of component (a) is about 0.01 to about 10 percent by weight of the solution or dispersion.

26. A method of cleaning a soiled article or surface, comprising contacting with said article or surface an aqueous solution or dispersion of a composition of matter represented by the structure

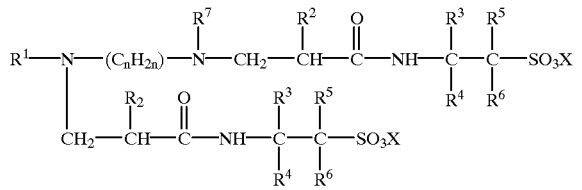

wherein n is 2 to 6; $R^1$ and $R^7$ are each independently hydrogen, hydrocarbyl groups, hydroxyhydrocarbyl groups, alkoxyhydrocarbyl groups, aminohydrocarbyl groups, aminohydrocarbyl groups wherein the amine nitrogen is substituted by

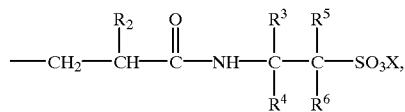

alkoxy-terminated or amine-terminated polyether groups, additional groups of the structure

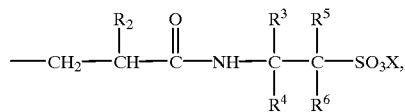

or mixtures thereof; $R^2$ through $R^6$ are each independently hydrogen or hydrocarbyl groups; and each X is independently hydrogen, metal, or ammonium or substituted ammonium.

27. The method of claim 26 wherein said soiled article or surface is a steel surface which is soiled with a soilant which comprises mineral oil.

* * * * *